(12) United States Patent
Wang et al.

(10) Patent No.: US 7,806,591 B2
(45) Date of Patent: Oct. 5, 2010

(54) ALIGNMENT APPARATUS FOR IMAGING SYSTEM USING REFLECTIVE ELEMENT

(75) Inventors: Xiaohui Wang, Pittsford, NY (US); David H. Foos, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 11/862,617

(22) Filed: Sep. 27, 2007

(65) Prior Publication Data

US 2009/0086927 A1 Apr. 2, 2009

(51) Int. Cl.
*A61B 6/08* (2006.01)
(52) U.S. Cl. ........................ 378/206; 378/196; 378/197; 378/198
(58) Field of Classification Search ............... 378/63, 378/162–166, 205, 206
See application file for complete search history.

(56) References Cited

U.S. PATENT DOCUMENTS

| | | | | |
|---|---|---|---|---|
| 2,955,205 | A | * | 10/1960 | Camfferman ............... 378/206 |
| 4,246,486 | A | * | 1/1981 | Madsen ..................... 378/206 |
| 4,752,948 | A | | 6/1988 | MacMahon |
| 4,836,671 | A | * | 6/1989 | Bautista .................... 356/3.1 |
| 5,241,578 | A | | 8/1993 | MacMahon |
| 5,388,143 | A | | 2/1995 | MacMahon |
| 5,517,546 | A | * | 5/1996 | Schmidt .................... 378/206 |
| 6,154,522 | A | | 11/2000 | Cumings |
| 6,422,750 | B1 | | 7/2002 | Kwasnick et al. |
| 6,851,851 | B2 | * | 2/2005 | Smith et al. ................ 378/189 |
| 7,014,362 | B2 | * | 3/2006 | Beimier et al. ............. 378/206 |
| 7,156,553 | B2 | | 1/2007 | Tanaka et al. |
| 2004/0258211 | A1 | * | 12/2004 | Scheuering ................ 378/206 |
| 2005/0047167 | A1 | * | 3/2005 | Pederson et al. ........... 362/542 |
| 2005/0057743 | A1 | * | 3/2005 | Seiffert .................... 356/138 |
| 2006/0183303 | A1 | * | 8/2006 | Inui et al. ................. 438/487 |
| 2008/0165933 | A1 | * | 7/2008 | Hornig ..................... 378/206 |

FOREIGN PATENT DOCUMENTS

WO    WO2006/094955 A1 *  9/2006

* cited by examiner

*Primary Examiner*—Hoon Song
*Assistant Examiner*—Mona M Sanei (57) ABSTRACT

An apparatus for aligning a radiation source with an image receiver has a first light source coupled to the radiation source and actuable to direct a first beam of light toward the image receiver and a second light source coupled to the radiation source and actuable to direct a second beam of light toward the image receiver. A reflector element is coupled to the image receiver and is disposed to form, when placed in the path of both first and second light beams, reflected light that indicates the relative alignment of the image receiver to the radiation source. The reflected light may form a pattern indicative of alignment.

17 Claims, 14 Drawing Sheets

ALIGNMENT APPARATUS FOR IMAGING SYSTEM USING REFLECTIVE ELEMENT

CROSS REFERENCE TO RELATED APPLICATIONS

This application is related to commonly assigned, copending U.S. patent applications (a) Ser. No. 11/834,234 filed Aug. 6, 2007 by Wang et al., entitled ALIGNMENT APPARATUS FOR IMAGING SYSTEM; (b) Ser. No. 11/862,579 filed Sep. 27, 2007 by Wang et al., entitled EXPOSURE CENTERING APPARATUS FOR IMAGING SYSTEM; and (c) Ser. No. 12/047,608 filed Mar. 13, 2008 by Wang et al., entitled ALIGNMENT APPARATUS FOR IMAGING SYSTEM.

FIELD OF THE INVENTION

This invention relates to apparatus for radiation imaging, having a positioning apparatus for providing proper centering alignment of the radiation source relative to an image detection device for recording a radiation image.

BACKGROUND OF THE INVENTION

When an x-ray image is obtained, there is generally an optimal angle between the radiation source and the two dimensional receiver that records the image data. In most cases, it is preferred that the radiation source provides radiation in a direction that is perpendicular to the surface of the recording medium of the receiver. For this reason, large-scale radiography systems mount the radiation source and the recording medium holder at a specific angle relative to each other. Orienting the source and the receiver typically requires a mounting arm of substantial size, extending beyond the full distance between these two components. With such large-scale systems, unwanted tilt or skew of the receiver is thus prevented by the hardware of the imaging system itself.

With the advent of portable radiation imaging apparatus, such as those used in Intensive Care Unit (ICU) environments, a fixed angular relationship between the radiation source and two-dimensional radiation receiver is no longer imposed by the mounting hardware of the system itself. Instead, an operator is required to aim the radiation source toward the receiver surface, providing as perpendicular an orientation as possible, typically using a visual assessment. In computed radiography (CR) systems, the two-dimensional image-sensing device itself is a portable cassette that stores the readable imaging medium. In direct digital radiography (DR) systems, the two-dimensional image-sensing device is a digital detector with either flat, rigid, or flexible substrate support.

There have been a number of approaches to the problem of providing methods and tools to assist operator adjustment of source and receiver angle. One classic approach has been to provide mechanical alignment in a more compact fashion, such as that described in U.S. Pat. No. 4,752,948 entitled "Mobile Radiography Alignment Device" to MacMahon. A platform is provided with a pivotable standard for maintaining alignment between an imaging cassette and radiation source. However, complex mechanical solutions of this type tend to reduce the overall flexibility and portability of these x-ray systems. Another type of approach, such as that proposed in U.S. Pat. No. 6,422,750 entitled "Digital X-ray Imager Alignment Method" to Kwasnick et al. uses an initial low-exposure pulse for detecting the alignment grid; however, this method would not be suitable for portable imaging conditions where the receiver must be aligned after it is fitted behind the patient.

Other approaches project a light beam from the radiation source to the receiver in order to achieve alignment between the two. Examples of this approach include U.S. Pat. No. 5,388,143 entitled "Alignment Method for Radiography and Radiography Apparatus Incorporating Same" and U.S. Pat. No. 5,241,578 entitled "Optical Grid Alignment System for Portable Radiography and Portable Radiography Apparatus Incorporating Same", both to MacMahon. Similarly, U.S. Pat. No. 6,154,522 entitled "Method, System and Apparatus for Aiming a Device Emitting Radiant Beam" to Cumings describes the use of a reflected laser beam for alignment of the radiation target. However, the solutions that have been presented using light to align the film or CR cassette or DR receiver are constrained by a number of factors. The '143 and '578 MacMahon disclosures require that a fixed Source-to-Image Distance (SID) be determined beforehand, then apply triangulation with this fixed SID value. Changing the SID requires a number of adjustments to the triangulation settings. This arrangement is less than desirable for portable imaging systems that allow a variable SID. Devices using lasers, such as that described in the '522 Cumings disclosure in some cases can require much more precision in making adjustments than is necessary.

Other examples in which light is projected from the radiation source onto the receiver are given in U.S. Pat. No. 4,836,671 entitled "Locating Device" to Bautista and U.S. Pat. No. 4,246,486 entitled "X-ray Photography Device" to Madsen. Both the Bautista '671 and Madsen '486 approaches use multiple light sources that are projected from the radiation source and intersect in various ways on the receiver.

Today's portable radiation imaging devices allow considerable flexibility for placement of the film cassette, CR cassette, or Digital Radiography (DR) receiver by the radiology technician. The patient need not be in a horizontal position for imaging, but may be at any angle, depending on the type of image that is needed and on the ability to move the patient for the x-ray examination. The technician can manually adjust the position of both the cassette and the radiation source independently for each imaging session. Thus, it can be appreciated that an alignment apparatus for obtaining the desired angle between the radiation source and the surface of the image sensing device must be able to adapt to whatever orientation is best suited for obtaining the image. Tilt sensing, as has been conventionally applied and as is used in the device described in U.S. Pat. No. 7,156,553 entitled "Portable Radiation Imaging System and a Radiation Image Detection Device Equipped with an Angular Signal Output Means" to Tanaka et al. and elsewhere, does not provide sufficient information on cassette-to-radiation source orientation, except in the single case where the cassette is level. More complex position sensing devices can be used, but can be subject to sampling errors and accumulated rounding errors that can grow worse over time, requiring frequent resynchronization.

Thus, it is apparent that conventional alignment solutions may be workable for specific types of systems and environments; however, considerable room for improvement remains. Portable radiography apparatus must be compact and lightweight, which makes the mechanical alignment approach such as that given in the '948 MacMahon disclosure less than desirable. The complex sensor and motion control interaction required by solutions such as that presented in the Tanaka et al. '553 disclosure would add considerable expense, complexity, weight, and size to existing designs, with limited benefits. Many less expensive portable radiation imaging units do not have the control logic and motion coordination components that are needed in order to achieve the necessary adjustment. None of these approaches gives the operator the needed information for making a manual adjustment that is in the right direction for correcting misalignment.

Importantly, none of these conventional solutions described earlier is particularly suitable for retrofit to existing portable radiography systems. That is, implementing any of these earlier solutions would be prohibitive in practice for all but newly manufactured equipment and could have significant cost impact.

Yet another problem not addressed by many of the above solutions relates to the actual working practices of radiologists and radiological technicians. A requirement for perpendicular delivery of radiation, imposed by some conventional alignment systems, is not optimal for all types of imaging. In fact, there are some types of diagnostic images for which an oblique (non-perpendicular) incident radiation angle is most desirable. For example, for the standard chest anterior-posterior (AP) view, the recommended central ray angle is oblique from the perpendicular (normal) by approximately 3-5 degrees. Conventional alignment systems, while they provide for normal incidence of the central ray, do not adapt to assist the technician for adjusting to an oblique angle.

Thus, it can be seen that there is a need for an apparatus that enables proper angular alignment of a radiation source relative to an image detection device for recording a radiation image.

SUMMARY OF THE INVENTION

An object of the present invention is to provide an alignment apparatus that is particularly suitable for a portable radiation imaging system. Accordingly, the disclosed apparatus is useful for aligning a radiation source with an image receiver; and comprises in one embodiment a first light source coupled to the radiation source and actuable to direct a first beam of light toward the image receiver; a second light source coupled to the radiation source and actuable to direct a second beam of light toward the image receiver; and a reflector element coupled to the image receiver and disposed to form, when placed in the path of both first and second light beams, a pattern of reflected light that indicates the relative alignment of the image receiver to the radiation source.

A feature of the apparatus is that it uses one or more patterns of light reflected back toward the radiation source from the receiver.

An advantage of the apparatus is that it allows straightforward retrofitting for existing x-ray apparatus.

A further advantage of the apparatus is that it provides a method that can be used with a variable SID distance.

These and other objects, features, and advantages of the present invention will become apparent to those skilled in the art upon reading the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION OF THE INVENTION

Figures shown and described herein are provided to illustrate principles of operation of embodiments of the present invention and are not drawn with intent to show actual size or scale. Some omission of conventional parts and exaggeration of detail have been used in order to emphasize important structural and positional relationships and principles of operation.

Figure 1:
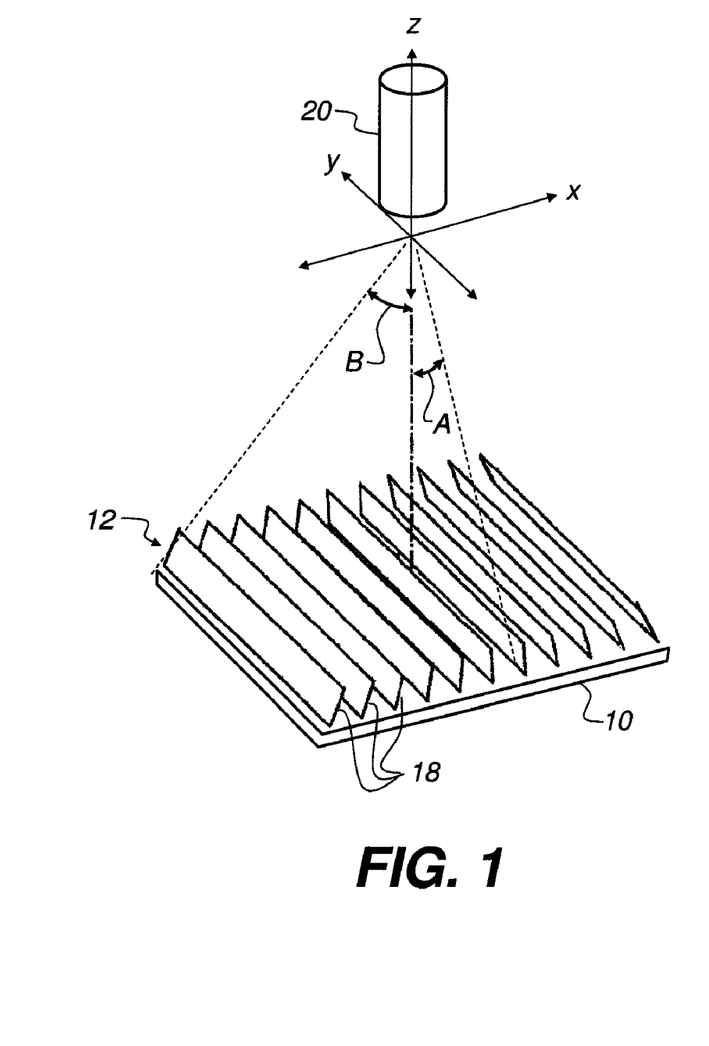
FIG. 1 is a schematic, perspective view showing how the antiscatter grid defines a focal plane at the proper Source-to-Image Distance (SID).

FIG. 1 shows angles and coordinates of interest for alignment of source to receiver. A radiation source 20 having an adjustable angular orientation is shown in position for directing radiation toward a receiver 10, such as a film cassette, CR cassette, or DR receiver. Receiver 10 may have a photostimulable medium, such as a film or phosphor medium, for example, or may have a detector array that records an image according to radiation emitted from radiation source 20. An antiscatter grid 12 has plates 18 arranged just above the surface of the receiver 10. Coordinate xyz axes are shown, with the source-to-image distance (SID) in the direction of the z axis. Angle A is in the yz plane, parallel to the length direction of grid 12 plates. Angle B is in the xz plane, orthogonal to the length direction of grid 12 plates. Angle A can vary over some range, since it is in parallel with grid 12 plates. Angle B, however, is constrained to a narrower range, typically within about ±5 degrees of normal.

Figure 2A:
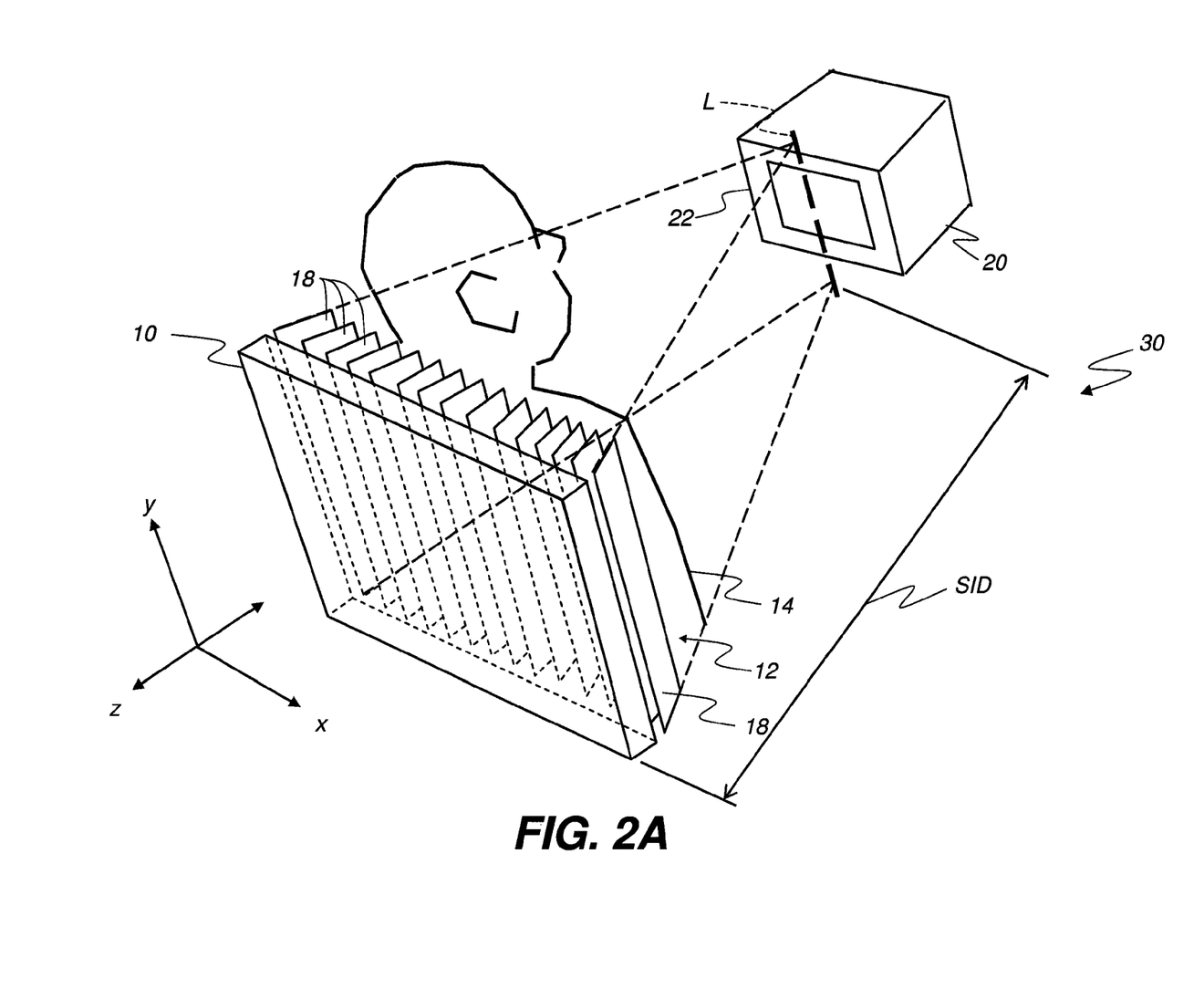
FIG. 2A is a perspective view showing the relative positions and dimensional relationships of the patient being imaged to basic components of a diagnostic imaging apparatus.

The perspective view of FIG. 2A shows components of a diagnostic imaging apparatus 30. Radiation source 20, such as an x-ray source, directs radiation toward a patient 14. Receiver 10, positioned behind the patient, forms the diagnostic image from the incident radiation passing through patient 14. Radiation source 20 has a collimator 22 that defines the radiation field that is directed toward receiver 10. Radiation source 20 has an adjustable angular orientation for directing radiation toward receiver 10. Here, the source-to-image distance (SID) is in the general direction of the z axis. Radiation source 20 is in its aligned position, at a suitable SID from receiver 10. Grid plates 18 are angularly arranged so that they define a focal line L where their respective planes converge at the SID. For best alignment, radiation source 20 should be centered near focal line L and have the face portion of collimator 22 generally parallel to the planar surface of receiver 10.

Figure 2B:
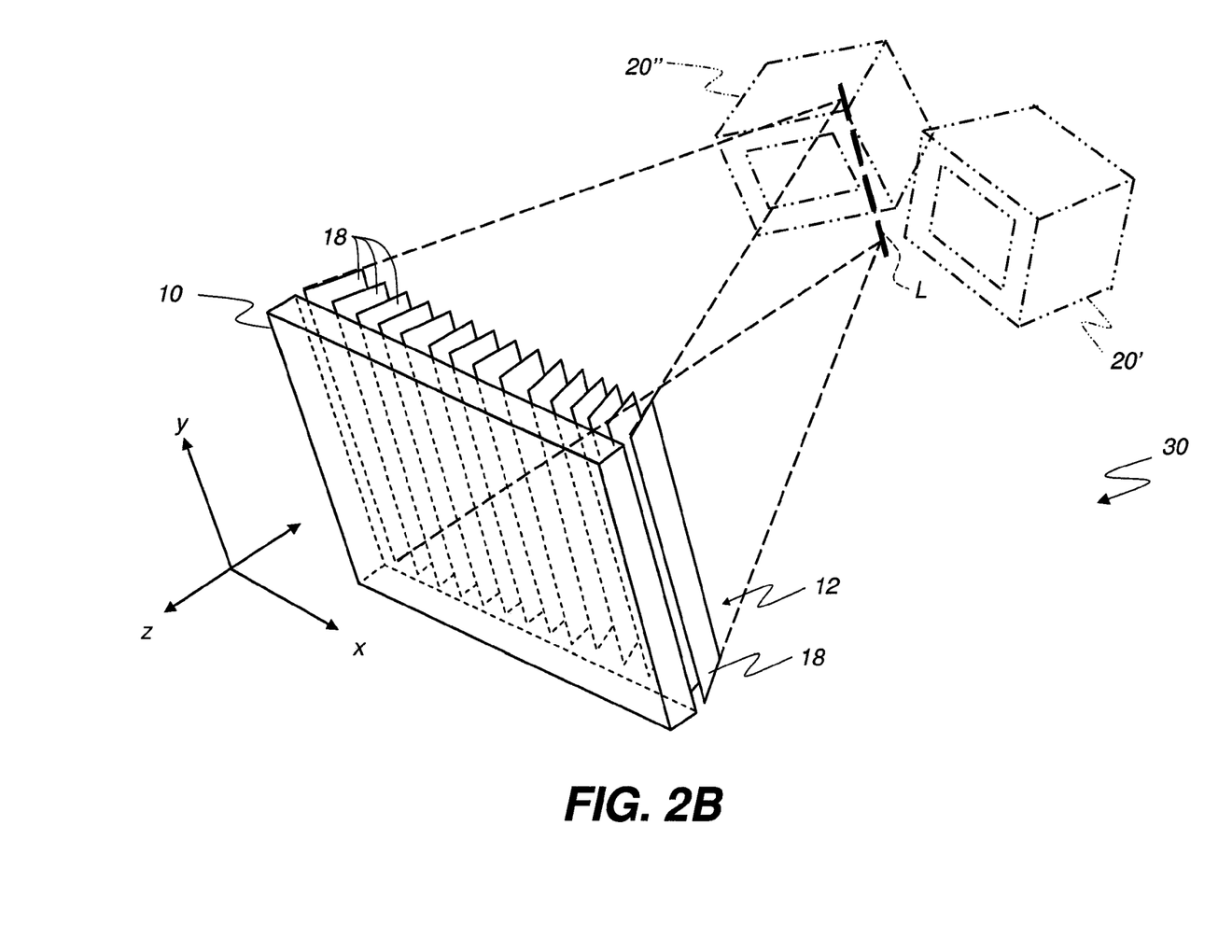
FIG. 2B is a perspective view showing exemplary out-of-alignment positioning.

FIG. 2B, by contrast, shows phantom outlines at 20' and 20" for poor positioning of radiation source 20. At positions 20' and 20", the SID is almost acceptable; however, radiation source 20 is not centered near focal line L and its angular orientation is badly skewed. Alignment of the radiation source with the grid would be poor at these and similar out-of-alignment positions, degrading image quality or, at worst, preventing a suitable diagnostic image from being obtained.

Figure 3A:
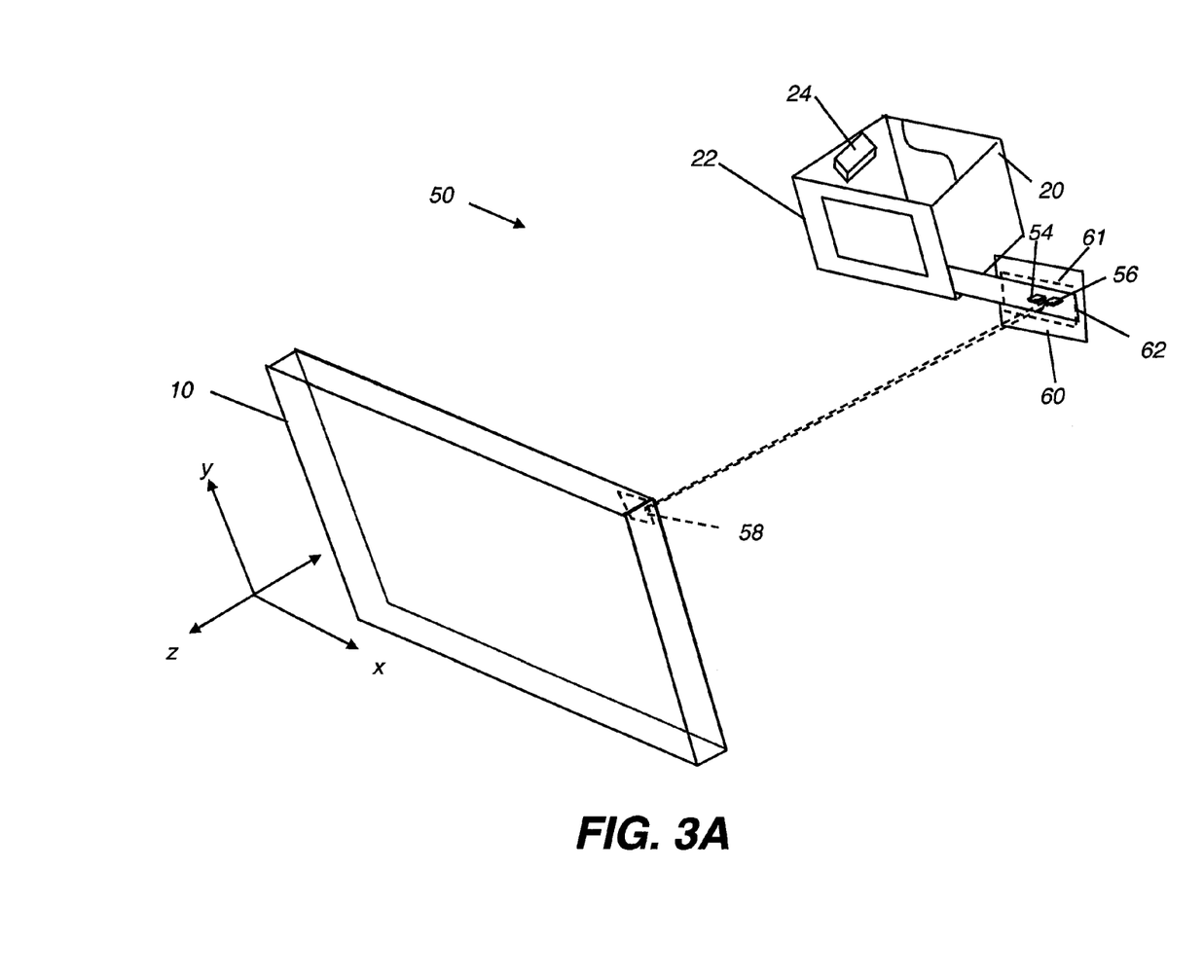
FIG. 3A is a perspective view showing the operation of one portion of an alignment apparatus in one embodiment.
Figure 3B:
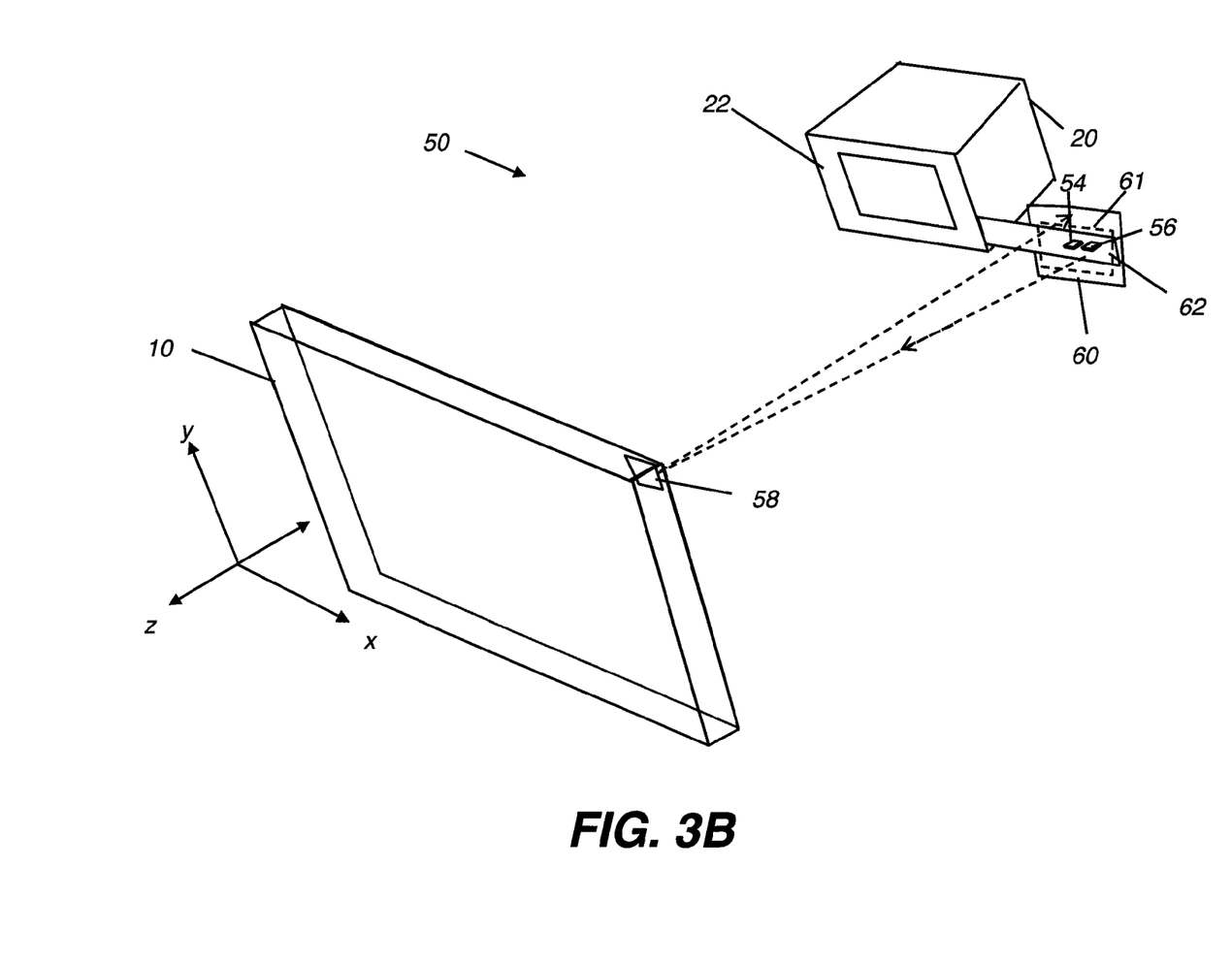
FIG. 3B is a perspective view showing the effects of slight mis-alignment on the reflected light.

In FIGS. 3A, 3B, 3C, 3D, and 3E grid 12 has been omitted for clarity and to show components of an alignment apparatus 50, by which alignment is obtained in embodiments of the present invention. Two or more light sources 54 and 56, are adapted to be coupled to radiation source 20 by an arm 62 or other mechanism, and can be actuated, that is, energized, in order to direct light toward receiver 10. A reflector element 58 is adapted to be coupled to receiver 10 to reflect this light back toward a defined target 60. Target 60 may be a separate component, such as a rectangular plate mounted to arm 62 as suggested in FIG. 3A. In one embodiment, target 60 is only partially opaque, allowing the operator to view the projected pattern from behind target 60. Target 60 may include a central area 61, shown in dashed lines, in which the presence of a reflected light pattern would indicate acceptable alignment. Alternately, target 60 may simply be a defined area on or near radiation source 20. For example, target 60 could be the area of arm 62 that is centered about light sources 54 and 56, as shown in FIG. 3A and in the top view of FIG. 4A, so that perfect alignment directs light back toward the source and no pattern of light is easily visible. The embodiment of FIGS. 3A and 4A shows target 60 in this position. In FIG. 3B, with the corresponding top view shown in FIG. 4B, slight misalignment of radiation source 20 relative to receiver 10 causes light from one or both light sources 54, 56 to be reflected to some point outside the desired central area of target 60. Target 60 could alternately be at some other convenient location, particularly at a position that is readily viewable to the operator when adjusting alignment.

Figure 3C:
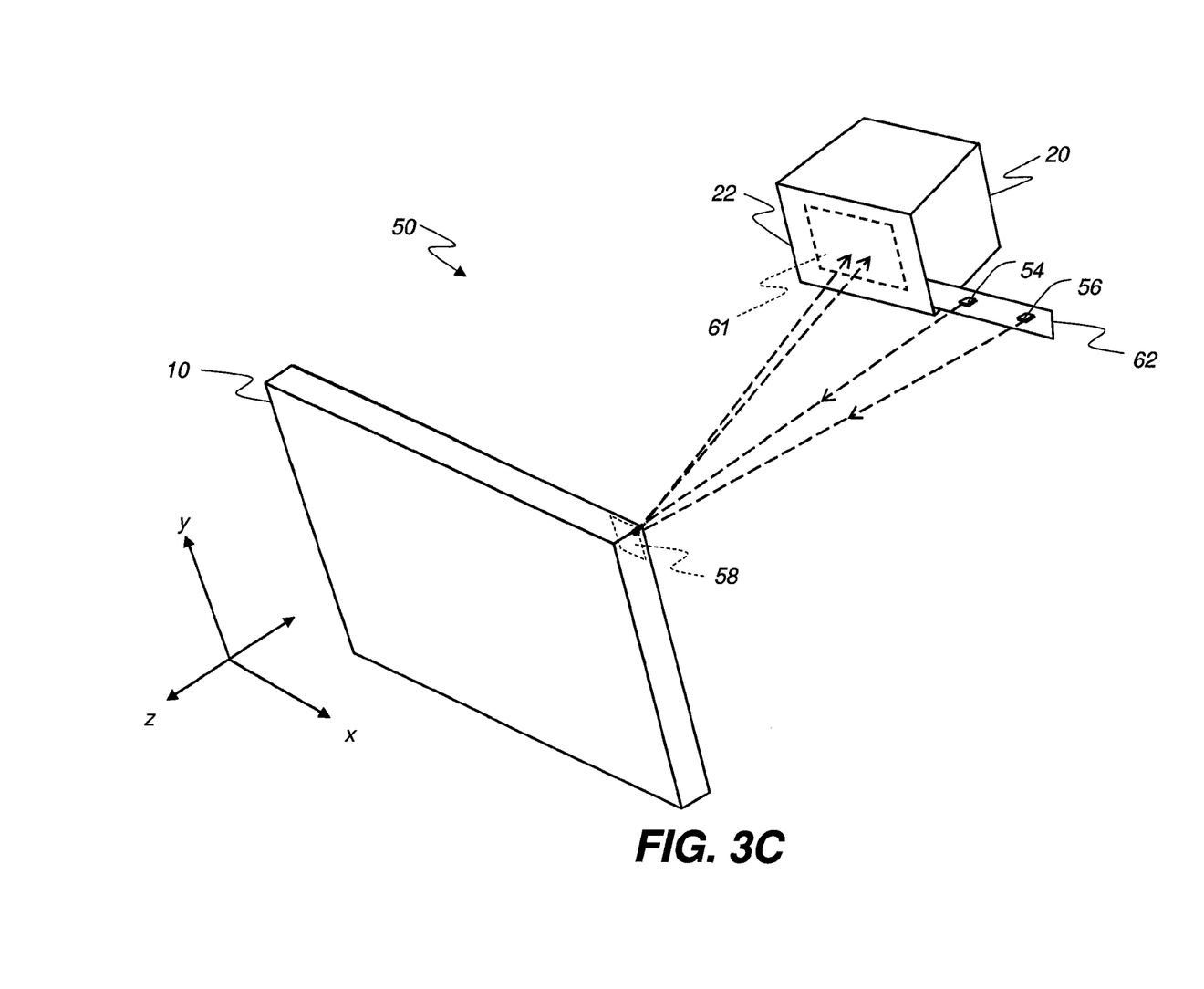
FIG. 3C is a perspective view showing the operation of the alignment apparatus in another embodiment.
Figure 3D:
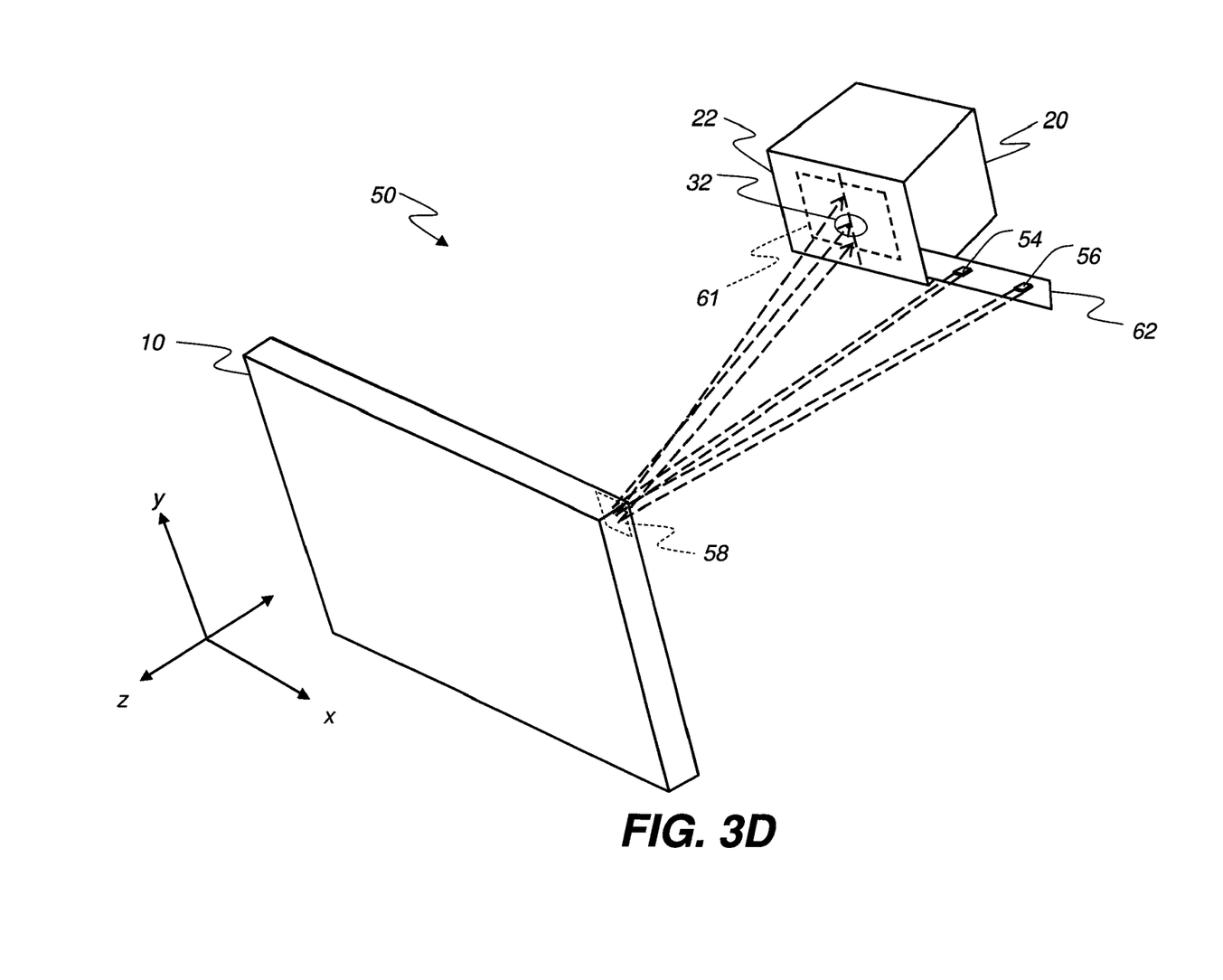
FIG. 3D is a perspective view showing the operation of one portion of an alignment apparatus in another alternate embodiment.
Figure 3E:
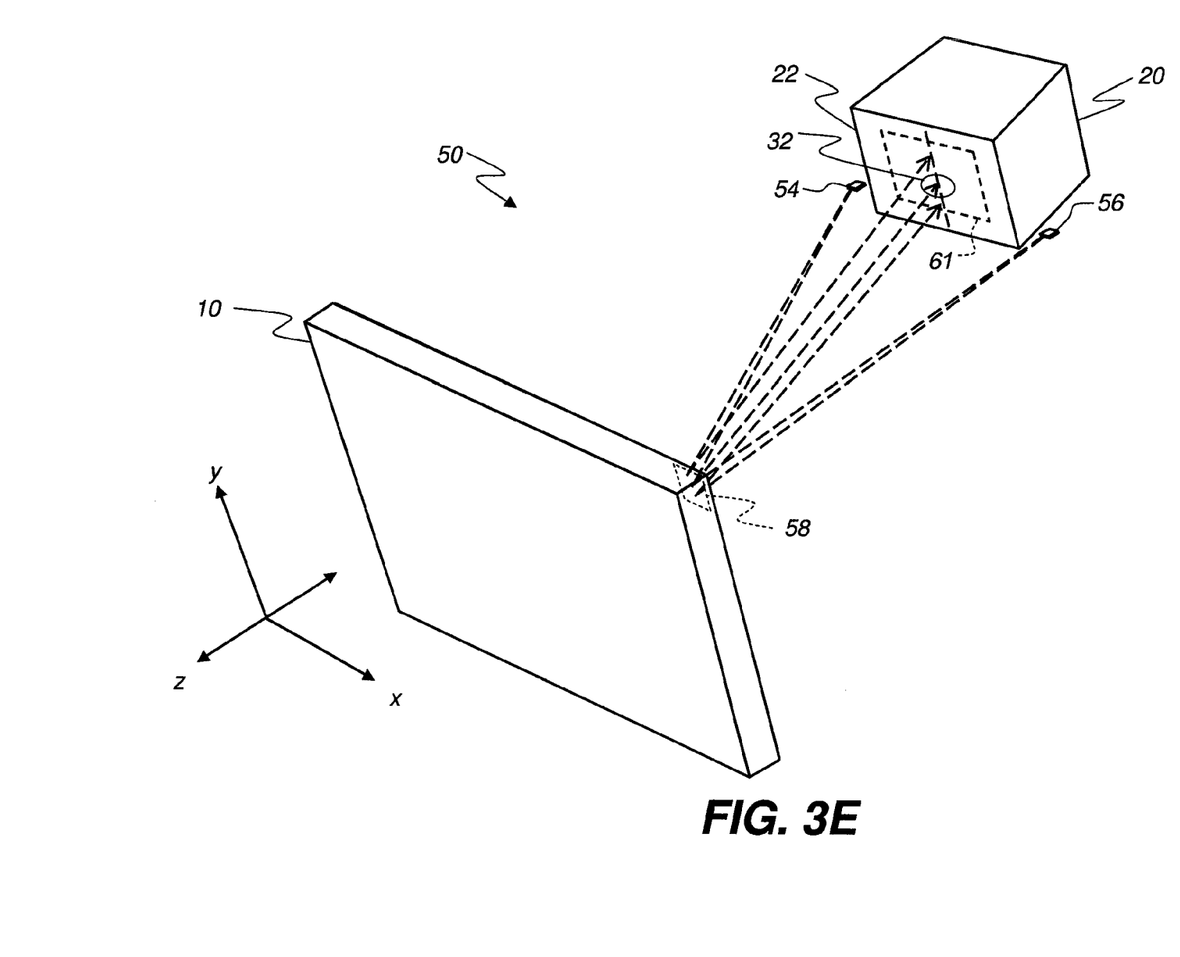
FIG. 3E is a perspective view showing the operation of another alternate embodiment that uses light sources placed on each side of the radiation source.
Figure 4A:
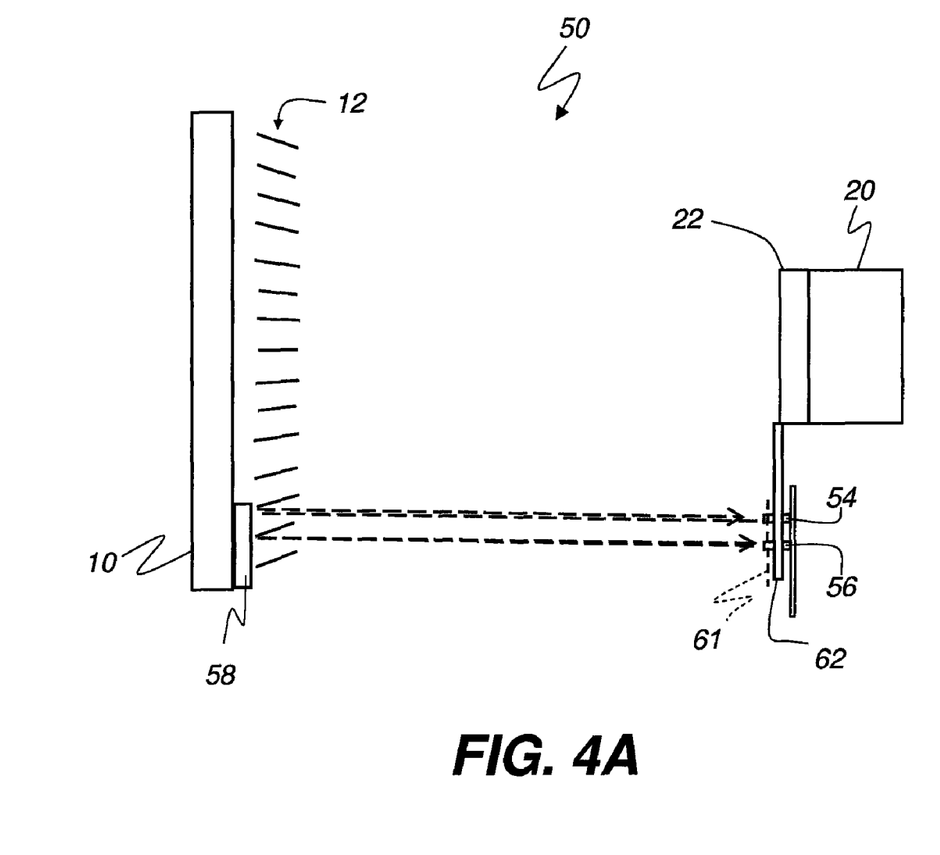
FIG. 4A shows a top view of apparatus operation corresponding to the embodiment shown in FIG. 3A.
Figure 4B:
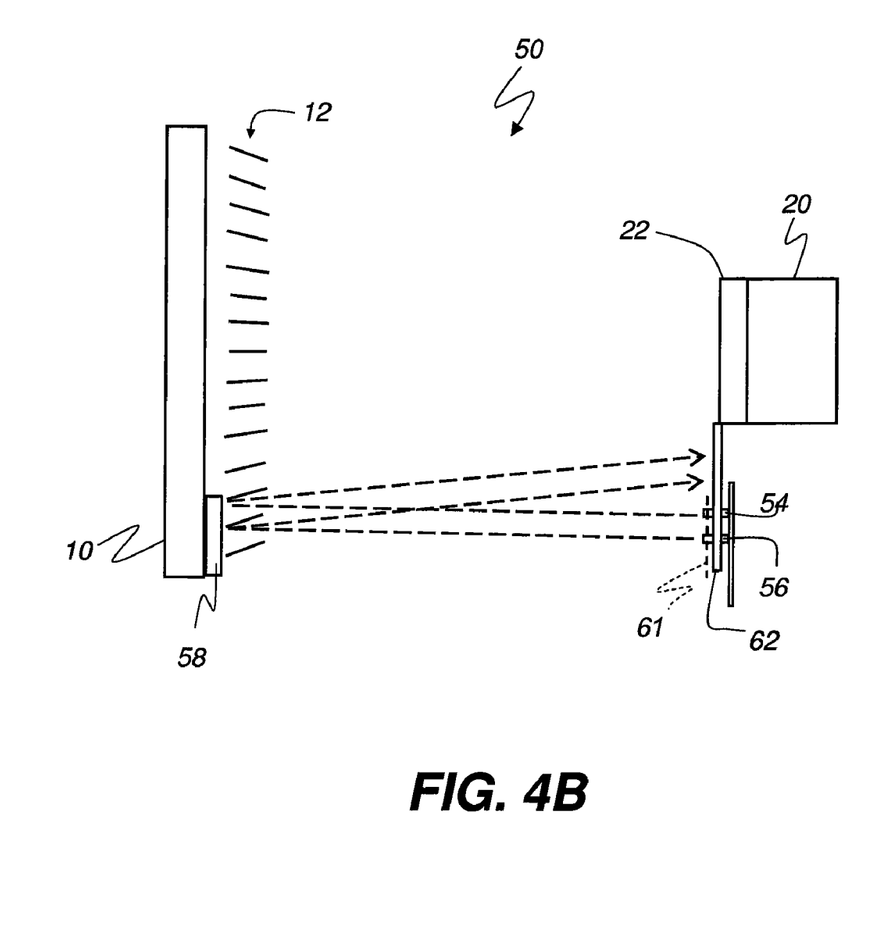
FIG. 4B shows a top view of apparatus operation corresponding to the embodiment shown in FIG. 3B.
Figure 4C:
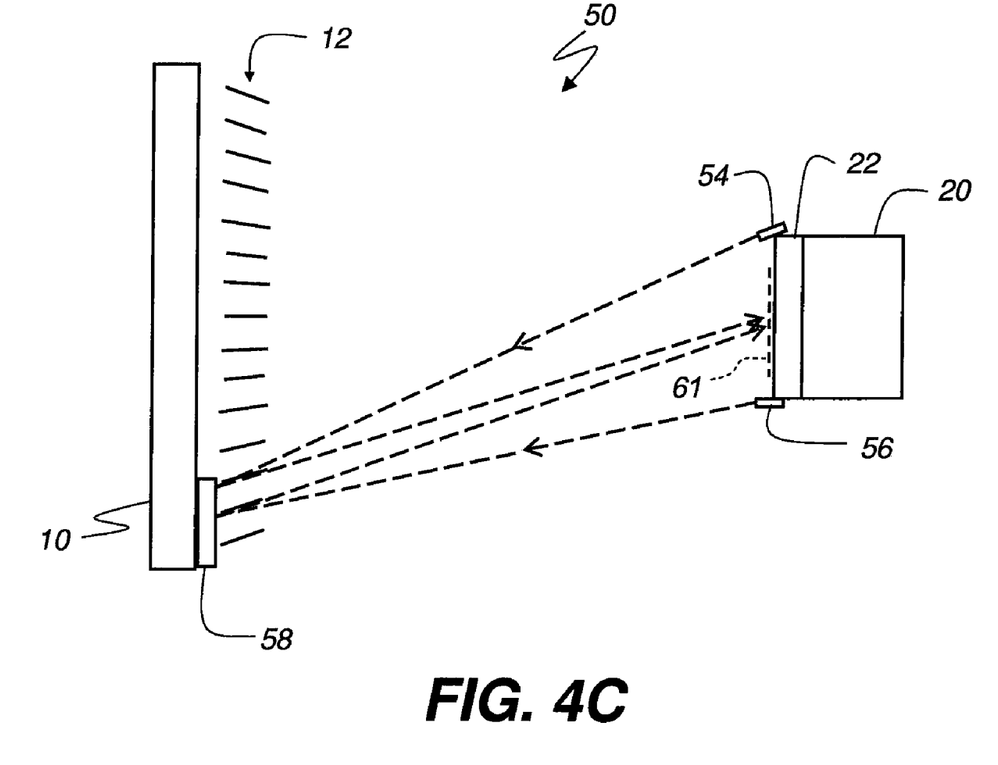
FIG. 4C shows a top view of apparatus operation corresponding to the embodiment shown in FIG. 3C.

FIG. 3C, with top view in FIG. 4C, shows an alternate embodiment of alignment apparatus 50 in which target 60 is defined as the front surface, typically the collimator surface, of radiation source 20. Good alignment is thus obtained when the pattern of light from light sources 54 and 56 is reflected by reflector element 58 and displays on the surface of radiation source 20. FIG. 3D shows an embodiment of alignment apparatus 50 in which the light reflected onto target 60 has a well-defined pattern, so that a vertical line is formed, for example. An indicium 32, or two or more indicia, can be part of the pattern projected from sources 54,56 or provided on the front surface of source 20, allowing adjustment directions and orientation to be more easily determined. A crosshairs or other symbol could be provided as indicium 32, for example. FIG. 3E shows an embodiment in which light sources 54 and 56 mount on opposite sides of radiation source 20 and use the front surface of collimator 22 as target 60.

Figure 5A:
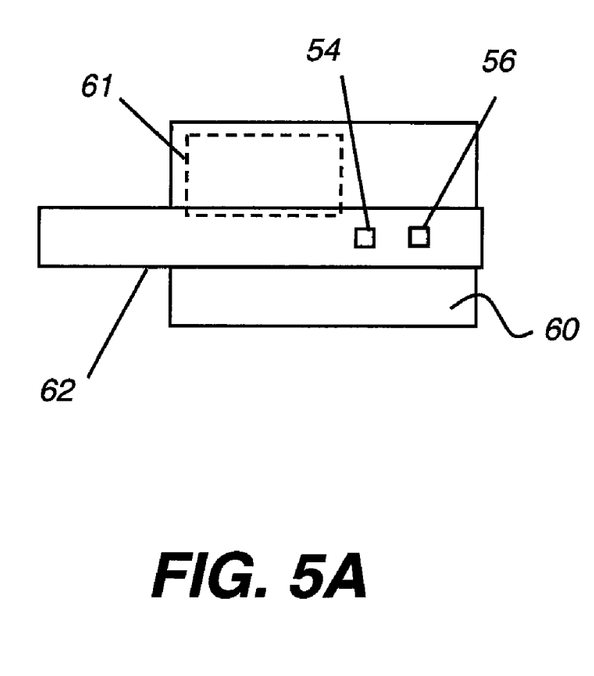
FIG. 5A shows a plan view of a light source having a target element in one embodiment.
Figure 5B:
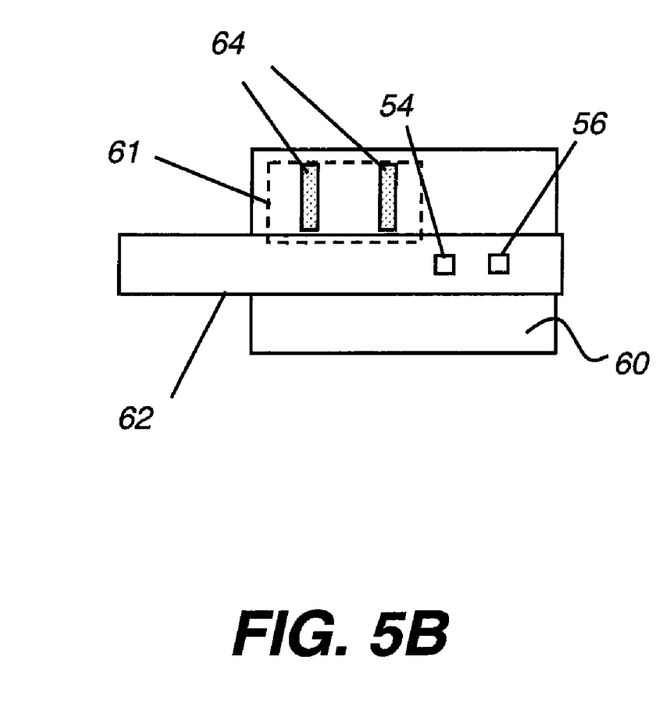
FIG. 5B shows a plan view of a target element with patterns from reflected light.

FIGS. 5A and 5B show a portion of arm 62 that contains target 60 as well as light sources 54 and 56 in one embodiment. FIG. 5A shows the de-energized state. Target 60 is defined toward the left of light sources 54 and 56 from this plan view. The energized state is shown in FIG. 5B. Here, a pattern 64 is obtained when light sources 54 and 56 are energized. With proper alignment conditions, pattern 64 appears as shown, fitting within the bounds of target 60.

Figure 5C:
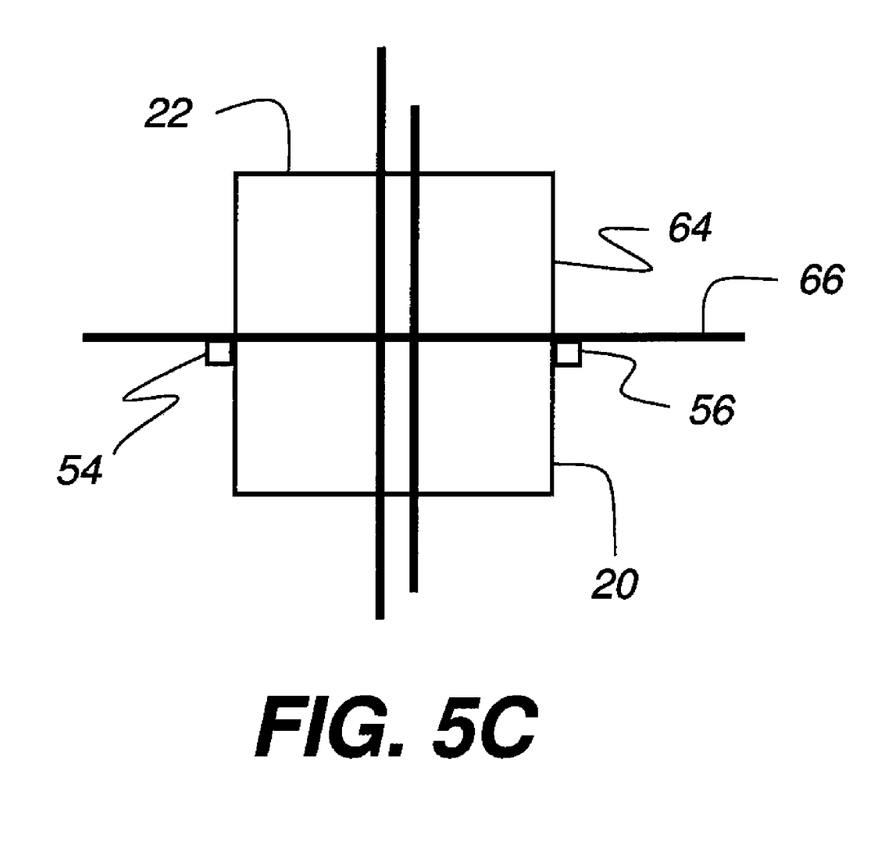
FIG. 5C shows a plan view of a target element with alternate patterns from reflected light.
Figure 6:
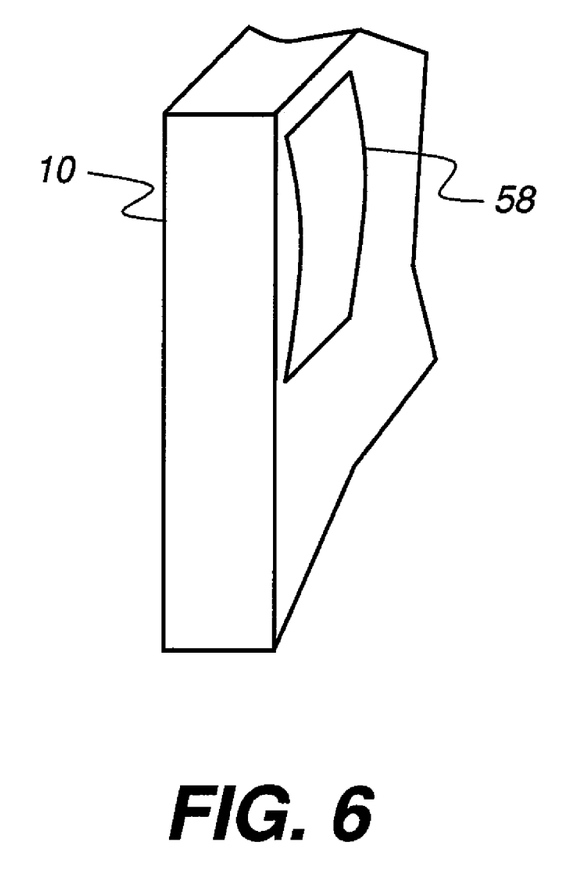
FIG. 6 is a perspective view of a reflector element coupled to a receiver in one embodiment.

The plan view of FIG. 5C shows a cross-hair pattern 66 that is reflected toward target 60 in one embodiment. This type of pattern, extended in two dimensions, can have advantages for improving vertical alignment of radiation source 20. Patterns with indicia or with two-dimensional extent can be obtained using lenses or other optical components in the illumination path from light sources 54 and 56. In addition, some shaping of the light can also be performed by reflector element 58. Referring to FIG. 6, there is shown a curved reflector 58 that would expand the reflected beam in the vertical direction, which can make the resulting pattern easier to see relative to target 60.

Unlike previous solutions to the problem of aligning receiver 10 to radiation source 20, the apparatus and method of embodiments of the present invention for forming patterns for alignment use reflector element 58 to redirect light back from receiver 10 and toward a predefined target 60 on or near the radiation source. Reflector 58 can be designed as part of receiver 10 or can be coupled to receiver 10 by its being fastened adhesively, magnetically, or by some other means, such as using flexible hook-and-loop or hook-and-pile connectors, such as VELCRO fasteners from Velcro Industries B.V., Amsterdam, NL. The apparatus and method of the present invention are compatible with the use of a grid and can be designed to provide a suitable SID that matches the focal distance of the grid.

A number of types of light sources 54 and 56 could be used. In one embodiment, low-power laser diodes direct light through lenses in order to form patterns on target 60. Alternately, light-emitting diodes (LEDs) or other solid-state sources could be employed, as well as filament-based bulbs and other light sources. Light sources could be pulsed or continuous.

In practice, some amount of initial calibration may be necessary to adapt alignment apparatus 50 to a particular radiography system. Referring to the top view of FIGS. 4A-4C, it can be appreciated that angular accuracy for light sources 54 and 56 is important for obtaining alignment at the intended SID. Light sources 54 and 56 can be adjusted during a calibration procedure that aligns pattern or patterns 64 (FIGS. 5B, 5C) at the proper SID and angular orientation for receiver 10. Light sources 54 and 56 could be designed to be adjusted or switched between two or more positions in order to be used with two or more different SIDs. Alternately, different pairs of light sources 54, 56 could be actuated for different SIDs or incident angles. Supporting lenses or other light-directing elements could be used in conjunction with light sources 54 and 56.

It is instructive to outline how alignment apparatus 50 is used by an operator. The following sequence is given by way of example:

1. Position the patient with respect to receiver 10.
2. Mount reflector 58 onto receiver 10.
3. Actuate light sources 54, 56. This can be done automatically, such as when the collimator light is energized, for example. A collimator light 24 is shown schematically in FIG. 3A. Alternately, light sources 54, 56 could be actuated by an operator action, such as setting a switch, or an instruction.

4. Move the radiation head into position so that pattern(s) 64 are reflected to appear within target 60.

5. Aim the collimator light onto the area of the patient that is to be imaged. Readjust as necessary, according to any shift in the position of the pattern.

6. Adjust collimator settings accordingly, using the collimator light as a guide. This step ensures that the radiation field is centered with respect to receiver 10 and that the field is left-right centered.

7. Obtain the image.

The apparatus and method of the present invention allow the operator to visually ascertain how well radiation source 20 is aligned with receiver 10 and to manually manipulate radiation source 20 into position until satisfactory alignment is achieved. As noted earlier, exact positioning is not a requirement for most diagnostic imaging environments; the operator can assess whether or not approximate alignment is close enough for obtaining the needed image. Automated methods, using sensors and control logic, could be used for obtaining alignment in an alternative embodiment. Importantly, the apparatus and method of the present invention do not require perpendicular radiation delivery, but instead allow some angular offset of radiation source 20 relative to a normal to the surface of receiver 10. Reflector 58 and light sources 54 and 56 can be adjusted to calibrate alignment for other than perpendicular incidence.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, any of a number of different methods could be used for coupling light sources 54 and 56 to radiation source 20, temporarily or permanently. Patterns 64 could have any number of arrangements for complementing each other to indicate alignment. Actuation of light sources 54 and 56 could be initiated in any of a number of ways, including by a command entered by the operator. A single light-emitting component could generate light that is then redirected into two separate paths to provide two light sources 54, 56 at separate locations, using optical fiber or other light guides, for example.

Thus, what is provided is an apparatus and method for providing proper centering alignment of the radiation source relative to an image detection device for recording a radiation image.

PARTS LIST

10 Receiver
12 Grid
14 Patient
18 Plates
20, 20', 20" Radiation source
22 Collimator
24 Collimator light
30 Imaging apparatus
32 Indicium
50 Alignment apparatus
54, 56 Light source
58 Reflector element
60 Target
61 Central area of target
62 Arm Pattern of reflected light
66 Cross-hairs pattern
A, B Angle
L Focal line
SID Source-to-Image Distance

The invention claimed is:

1. An apparatus for aligning an image receiver with a radiation source having a collimator light for aiming the source at an area to be imaged, the apparatus comprising:
    a first light source adapted to be coupled to the radiation source and actuable to direct a first beam of light toward the image receiver;
    a second light source adapted to be coupled to the radiation source and actuable to direct a second beam of light toward the image receiver;
    a reflector element adapted to be coupled to the image receiver and disposed to form, when placed in the path of both first and second light beams, reflected light that indicates the relative alignment of the image receiver to the radiation source; and
    a target adapted to be coupled to the radiation source to receive the reflected light,
    whereby the received reflected light on the target is visually observable by an operator to provide the operator a readily viewable indication of the relative alignment of the image receiver and the radiation source when the collimator light is aimed at the area to be imaged.

2. The apparatus of claim 1 wherein at least one of the first and second light sources is a laser.

3. The apparatus of claim 1 wherein the first and second light sources are on opposite sides of the radiation source.

4. The apparatus of claim 1 wherein at least one of the first and second light sources is an LED.

5. The apparatus of claim 1 wherein at least one of the first and second light sources is a pulsed light source.

6. The apparatus of claim 1 wherein the reflector element is disposed to form a pattern of reflected light on the target.

7. The apparatus of claim 1 wherein the target is adapted to be coupled to a structure mounted on the radiation source and the target is partially opaque, thereby allowing the operator to view the reflected light from behind the target.

8. The apparatus of claim 1 wherein the first light source is actuated when the collimator light is energized.

9. The apparatus of claim 1 wherein the reflector element has a curved surface.

10. An apparatus for aligning an image receiver with a radiation source having a collimator light for aiming the source at an area to be imaged, the apparatus comprising:
    a first light source coupled to the radiation source and actuable to direct a first beam of laser light toward the image receiver;
    a second light source coupled to the radiation source and actuable to direct a second beam of laser light toward the image receiver;
    a target mounted on or forming part of a visible surface of the radiation source; and
    a reflector element coupled to the image receiver and disposed to form, when placed in paths of both the first and the second laser light beams, reflected light on the target, wherein the reflected light is visually observable by an operator and indicates the relative alignment of the image receiver to the radiation source when the collimator light is aimed at the area to be imaged.

11. The method of claim 10, wherein the reflector element is disposed to form a pattern of reflected light on the target.

12. A method for aligning an image receiver with a radiation source having a collimator light for aiming the source at an area to be imaged, the method comprising:
    directing a first light beam toward the image receiver from a first light source coupled to the radiation source;

directing a second light beam toward the image receiver from a second light source coupled to the radiation source;

reflecting the first and second beams back toward the radiation source, thereby forming reflected light that indicates the relative position of the image receiver to the radiation source;

receiving the reflected light on a target mounted on or forming part of a visible surface of the radiation source, wherein the reflected light is visually observable visually by an operator;

viewing the reflected light on the target by the operator; and repositioning the radiation source and the first and second light sources to achieve a desired alignment between the radiation source and the image receiver as indicated by the reflected light received and viewed by the operator on the target when the collimator light is aimed at the area to be imaged.

13. The method of claim 12 wherein reflecting the first and second beams comprises providing a reflector element that is coupled to the image receiver.

14. The method of claim 12 wherein reflecting the first and second beams comprises providing a reflector element that is coupled to the image receiver and has a curved surface.

15. The method of claim 12 wherein directing the first light beam comprises actuating a solid-state light source.

16. The method of claim 12, wherein the reflector element is disposed to form a pattern of reflected light on the target.

17. The method of claim 12, further comprising:

following the reorienting, aiming the collimator light at the area to be imaged; and following the aiming, again repositioning the radiation source and the light sources to maintain the desired alignment.

* * * * *